(12) United States Patent
Fukumoto

(10) Patent No.: US 9,622,842 B1
(45) Date of Patent: Apr. 18, 2017

(54) RODENT IMMOBILIZATION APPARATUS AND METHOD OF USE THEREOF

(71) Applicant: Jutaro Fukumoto, Tampa, FL (US)

(72) Inventor: Jutaro Fukumoto, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/198,192

(22) Filed: Jun. 30, 2016

Related U.S. Application Data

(60) Provisional application No. 62/278,680, filed on Jan. 14, 2016.

(51) Int. Cl.
    *A01K 1/06*     (2006.01)
    *A61D 3/00*     (2006.01)
    *A61B 16/00*     (2006.01)

(52) U.S. Cl.
    CPC .............. *A61D 3/00* (2013.01); *A01K 1/0613* (2013.01); *A61B 16/00* (2013.01)

(58) Field of Classification Search
    CPC ........ A01K 1/03; A01K 1/031; A01K 1/0613; A61D 3/00; A61D 2003/006; A61D 2003/003
    USPC ................. 119/724–726, 751–753, 755–757, 119/809–820, 833, 856; 5/600, 601, 603, 5/610, 621, 622, 623, 624, 637, 647, 650
    See application file for complete search history.

(56) References Cited

U.S. PATENT DOCUMENTS

| | | | | |
|---|---|---|---|---|
| 1,398,484 A | * | 11/1921 | Holding | ................... A61D 3/00 119/752 |
| 2,279,012 A | * | 4/1942 | Packchanian | ............ A61D 3/00 119/755 |
| 2,832,313 A | * | 4/1958 | Toepel | ................... A01K 15/00 119/755 |
| 2,987,042 A | | 6/1961 | Rothberg | |
| 3,103,204 A | * | 9/1963 | Greene | ................ A01K 1/0613 119/751 |
| 3,130,709 A | | 4/1964 | Rothberg | |

(Continued)

FOREIGN PATENT DOCUMENTS

CN             201734800 U       2/2011

OTHER PUBLICATIONS

Machine English translation of CN 201734800.

*Primary Examiner* — Thien Thanh Pham
(74) *Attorney, Agent, or Firm* — Nilay J. Choksi; Smith & Hopen, P.A.

(57) ABSTRACT

A rodent immobilizing apparatus for use during experimental procedures, dissection, and sample procurement. The apparatus has two (2) points of adherence to the dissection board, one at the head/jaw region and one at the tail region. Generally, the rodent immobilizing apparatus includes a base, a bed positioned atop the base, a bank disposed along one side of the bed, another bank disposed along the opposite side of the bed, a string/wire hook affixed to each bank with string/wire therebetween, and a tail clip/clamp positioned at an inferior portion of the bed. The bed is slidable along the banks to accommodate different sized rodents. In operation, an anesthetized/euthanized rodent is positioned supine on the bed. The bed slides along the banks, so that the string/wire is hooked within the rodent's jaw. The tail is clamped to the bed, and the bed is pulled back to stretch out the rodent, thus immobilizing the rodent completely and rapidly.

9 Claims, 17 Drawing Sheets

(56) References Cited

U.S. PATENT DOCUMENTS

| | | | |
|---|---|---|---|
| 3,286,694 A | | 11/1966 | Landy |
| 3,484,096 A | * | 12/1969 | Briggs ..................... A61D 3/00 119/755 |
| 4,214,556 A | * | 7/1980 | Knox ....................... A61D 3/00 119/754 |
| 4,261,295 A | | 4/1981 | Kanetake et al. |
| 4,459,941 A | * | 7/1984 | Moffatt ................... A61D 3/00 119/722 |
| 4,779,858 A | * | 10/1988 | Saussereau .......... A61B 6/0421 378/209 |
| 5,329,934 A | * | 7/1994 | Bowman ................ A47D 13/08 128/870 |
| 5,385,119 A | * | 1/1995 | Tarulli .................... A61D 3/00 119/755 |
| 5,915,334 A | * | 6/1999 | Cummings .............. A61D 3/00 119/723 |
| 6,077,221 A | * | 6/2000 | Fowler, Jr. ......... A61B 17/0293 434/262 |
| 6,675,741 B2 | | 1/2004 | Remmler |
| 6,789,510 B1 | | 9/2004 | Lee |
| 8,028,663 B2 | * | 10/2011 | Chen .................... A01K 1/0613 119/729 |
| 2006/0042561 A1 | * | 3/2006 | Wang ................... A01K 13/001 119/753 |
| 2016/0175079 A1 | * | 6/2016 | Adamo ................. A61M 11/00 128/203.14 |

\* cited by examiner

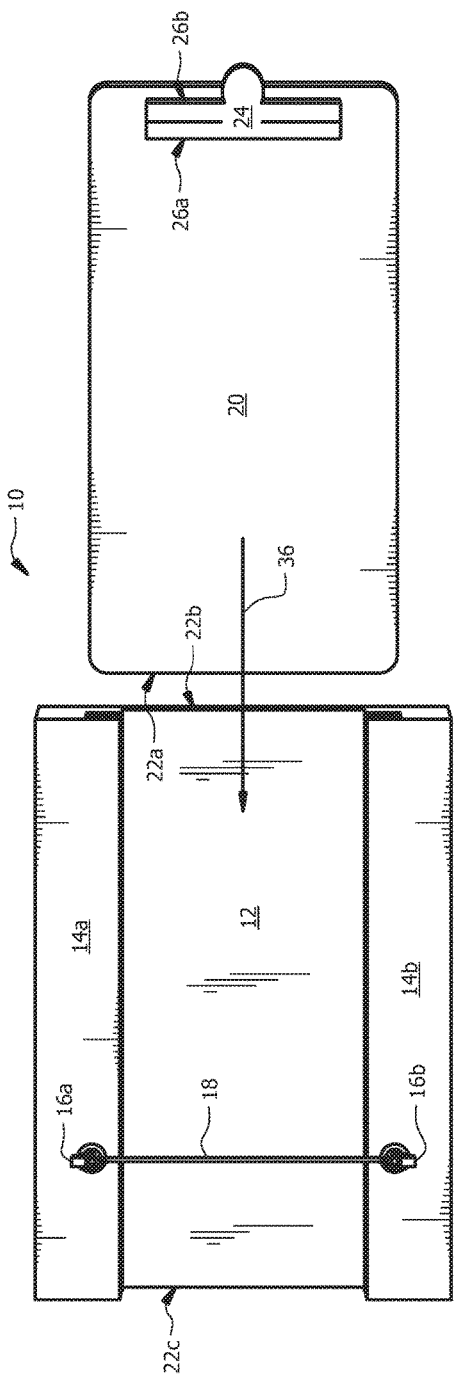
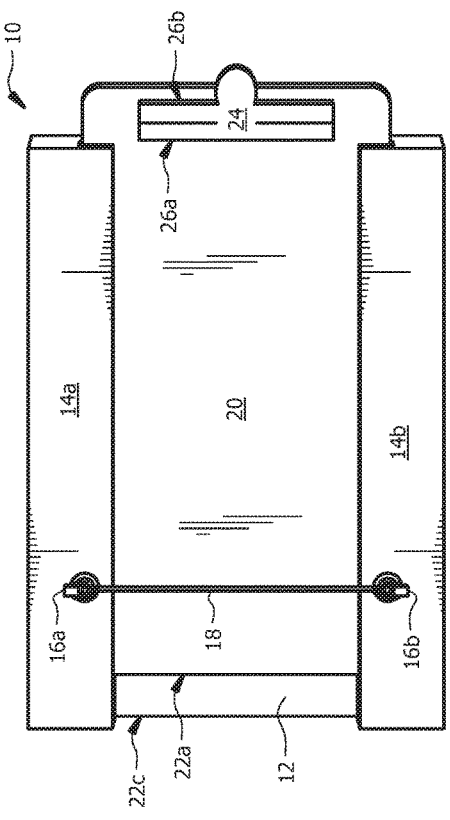
FIG. 3A
FIG. 3B

RODENT IMMOBILIZATION APPARATUS AND METHOD OF USE THEREOF

CROSS-REFERENCE TO RELATED APPLICATIONS

This nonprovisional application claims priority to U.S. Provisional Patent Application No. 62/278,680, entitled "Rodent Immobilization Apparatus and Method of Use Thereof", filed Jan. 14, 2016 by the same inventor, the entirety of which is incorporated herein by reference.

BACKGROUND OF THE INVENTION

1. Field of the Invention

This invention relates, generally, to apparatuses that facilitate dissection of an experimental animal. More specifically, it relates to rodent-stabilizing dissection devices.

2. Brief Description of the Prior Art

Rodents, and in particular mice, are by far the most widely used animals in biomedical research. The speed at which the dissection of mice is performed can make or break the results of the animal experiments in basic research.

Securing the hands and feet of an anesthetized and/or euthanized rodent on a dissection board by tapes or pins is the most widely adopted method for facilitating survival or non-survival rodent surgery and postmortem sample collection (see FIG. 1). However, this securing step takes a particular amount of time and is tedious. Not only is taping/pinning the limbs time-consuming, but removing the tapes/pins from the board after each dissection is also time-consuming. Even a small delay in this securing step can compromise the integrity and reproducibility of animal experiments or even ruin the entire research projects, especially when (i) a large number of rodents need to be dissected in a relatively short time period (e.g., after each rodent dissection is done, the dissector has to remove all the pins and tapes to clean up the board and prepare for the next one); (ii) the biological samples to be collected degrade quickly after anesthesia and/or euthanasia; (iii) time-sensitive procedures such as blood collection or vascular perfusion are to be performed; and/or (iv) the conditions of the animal to be dissected worsen every second and minute due to the preceding treatments.

In particular, the quality of biological samples-especially unstable components such as mRNA, protein, cytokine, and hormone-worsen every second. The levels of mRNAs, cytokines, other physiologically active substances, and/or the histopathological manifestation of each organ are easily affected by the dramatic hemodynamic alterations caused by anesthesia and/or method of euthanasia. Thus, expediting rodent dissection is a critical shortcut to a successful animal experiment. FIG. 2 depicts the general timeline between euthanasia and sample collection, showing that the time period should be as short as possible to preserve samples that may quickly degrade (e.g., RNA, cytokines, heart tissue) and to uphold statuses that quickly change (e.g., cell viability, inflammation in organs, and necrosis of organs).

Further, if the rodent to be dissected is not securely immobilized, a situation may well arise where every time the dissector grabs/pulls/cuts the skin or organs of the rodent on the dissection board, the body of the rodent passively moves. This movement inevitably causes a disturbance for the dissector and can even provoke such a mishandling by the dissector irreparable sample damage results.

Attempts have been made to stabilize experimental animals during dissection. Examples include, but are not limited to, Chinese Publication No. CN 201734800 U; U.S. Pat. No. 2,987,042; U.S. Pat. No. 3,130,709; U.S. Pat. No. 3,286,694; U.S. Pat. No. 4,261,295; U.S. Pat. No. 6,675,741; and U.S. Pat. No. 6,789,510. However, the conventional art, including the forgoing references, is still excessively time-consuming and does not provide the appropriate immobilization needed for dissection.

Accordingly, what is needed is a dissection device that provides rapid but sufficient immobilization of the experimental rodents, thereby (i) accelerating surgical procedures and sample collection and (ii) helping to preserve and maintain accurate experimental conditions and results. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved rodent immobilization apparatus and method of use thereof is now met by a new, useful, and nonobvious invention.

In an embodiment, the current invention is a rodent immobilization apparatus for survival or non-survival surgical procedures on rodents, as well as postmortem sample collection from euthanized rodents. The apparatus includes a first bank and a second bank each having a straight inner edge that are disposed a horizontal spaced distance away from each other, thus forming an empty area therebetween. The inner edges of the banks are substantially parallel to each other. Each bank also includes an overhang component (e.g., flange) that extends toward each other in the empty area. A hook or clamp module is positioned above each bank, and the hooks/clamps are disposed in diametric opposite each other across the empty area. A string or wire is secured on the hook/clamp modules and extends sufficiently taut across the empty area, substantially perpendicular to the length of the banks. This forms a vertical spaced distance between the string/wire and a surface on which the banks are positioned. This surface may be the top surface of a base component disposed in underlying relation to the banks.

The apparatus further includes a flat bed component having a width that is slightly smaller than a width of the empty area, such that the bed component is slidable along the inner edges of the banks with the overhang component disposed in overlying relation to each side of the bed component, thus creating additional interfaces between the bed component and the banks to stabilize the bed component between the banks. A tail clamp is disposed on an inferior portion of the bed component. The tail clamp has an open superior side and an open inferior side. Optionally, the tail clamp may have an inherent downward bias relative to the bed component to hold the rodent's tail in place. In this case, the rodent's tail would be positioned within the clamp when a forces acts on the clamp to overcome the bias, and the clamp immobilizes the tail when the force is removed. The apparatus further includes a string-to-clamp distance formed between the string/wire and the tail clamp, where the string-to-clamp distance and the rodent's size have a direct relationship to each other, such that as the rodent's size increases, the string-to-clamp distance increases as well.

The bed component is configured to receive a rodent thereon, the string/wire is configured to hook into a tooth of the rodent, and the tail clamp is configured to receive the tail of the rodent through its open sides to immobilize the rodent's tail. In operation, when the rodent is positioned on the bed component, when the string/wire is hooked into the rodent's jaw/tooth, and when the tail clamp is immobilizing the rodent's tail, the bed component can slide inferiorly to stretch the rodent on the bed component.

In certain embodiments, the apparatus is modular in nature, such that the base component, the banks, the hooks/clamps, the string/wire, and the bed component are all separable from each other. This way, if one component becomes damaged, it can be removed and replaced easily.

In other embodiments, each hook/clamp module can be a column with a vertical channel disposed therethrough and a plurality of horizontally-extending, vertically-spaced divots extending from the vertical channel, such that the string/wire can be secured within one of those divots. Optionally, a ring on each end of the string/wire can be used to facilitate securement within the divots. A top divot may be a large window through which the string or wire can be threaded.

In a separate embodiment, the current invention is a method of dissecting multiple rodents and collecting biological samples from them in an assembly line. Two (2) banks are provided, each with a hook/clamp module secured in overlying relation thereto, where the banks are positioned a horizontal spaced distance away from each other, thus forming an empty area therebetween. The hook/clamp modules are disposed in diametric opposite each other across the empty area. The banks also have inner edges that are substantially parallel to each other along the empty area. The banks each include an overhang component (e.g., flange) that extends toward each other in the empty area. A string or wire is secured sufficiently taut between the hooks/clamps, such that the string/wire extends across the empty area in a direction substantially perpendicular to a length of the banks. The string/wire is positioned a vertical spaced distance above the surface on which the banks are disposed. This surface may be the top surface of a base component disposed in underlying relation to the banks.

A flat bed component is also provided, where the bed component has a tail clamp secured thereto on an inferior portion thereof. The width of the bed component is slight smaller than the width of the empty area. The tail clamp has an open superior side and an open inferior side. Optionally, the tail clamp may have an inherent downward bias relative to the bed component to hold the rodent's tail in place. In this case, the step of securing the rodent's tail in the tail clamp is performed by applying a force onto the tail clamp to overcome the bias. The rodent's tail would then be positioned within the clamp, and the clamp immobilizes the tail against the bed component when the force is removed.

A rodent is positioned supine on the bed component with a tail of the rodent extending toward the inferior portion of the bed component. The bed component is slid along the inner edges of the banks and under the overhangs of the banks. The rodent's jaw is aligned with the string/wire, and the string/wire is hooked into the rodent's jaw. The rodent's tail is secured in the tail clamp through its open sides, and the bed component is slid inferiorly to stretch out the rodent on the bed component with the string/wire hooked into the rodent's jaw and the tail clamp immobilizing the rodent's tail. Regardless of the order of the steps used to accomplish the foregoing, the surgical procedure and/or sample collection can then be performed on the rodent.

In certain embodiments, if more than one rodent is to be dissected or a sample is to be collected therefrom, the current rodent's jaw is unhooked from the string/wire, and the bed component is slid inferiorly out of the banks. Subsequently, a second bed component with its own tail clamp is provided and is substantially similar to the initial bed component and tail clamp. A second rodent that has been anesthetized or euthanized is positioned supine on the second bed component with its tail extending toward the inferior portion of the second bed component. Similar to the first rodent, the second bed component is slid along the inner edges of the banks under the overhang components. The second rodent's jaw is aligned with the string/wire, and the string/wire is hooked into the rodent's jaw. Its tail is secured in the tail clamp, and the second bed component is slid inferiorly to stretch the second rodent on the second bed component with the wire/string hooked into the jaw and the tail clamp immobilizing the tail. At this point, the surgical procedure and/or sample collection can be performed.

In a further embodiment where there are multiple dissections and/or sample collections, a string-to-clamp distance between the string/wire and the second tail clamp can be adjusted, where the string-to-clamp distance and the rodent's size have a direct relationship to each other. As such, the string-to-clamp distance would be increased when the second rodent has a larger size than the first rodent, and conversely, the string-to-clamp distance would be decreased when the second rodent has a smaller size than the first rodent.

If the rodent immobilization apparatus includes the columnar hook/clamp module, as previously discussed, the string/wire can be secured within each hook/clamp module by securing the string/wire in one of the divots in each module. This may be done by threading the string/wire through a topmost divot, which may be a large window. This can also be facilitated by including a ring on each end of the string/wire for engaging the desired divots.

In a separate embodiment, the current invention is a rodent immobilization apparatus or a method of dissecting or collecting samples from a plurality of rodents, comprising any one or more—or even all—of the foregoing features.

It can be understood by one of ordinary skill in the art that the steps of the foregoing methodology can be interchanged or performed out of order, with the ending result of the rodent immobilized on the bed component still being accomplished.

It is an object of the current invention to provide a rodent dissection device that provides a level of ease and versatility not currently seen in the art. This versatility is primarily achieved with the ability to adjust the string-to-clamp length to the size of the mouse by only moving the bed and/or by moving the banks. This allows the device to be used for mice of different sizes, i.e., from small young mice to huge aged mice.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 3A is a top view of an embodiment of the current invention with the bed component separated from the main board component.

FIG. 3B is a top view of the embodiment of FIG. 3A with the bed component engaged with the main board component.

DETAILED DESCRIPTION OF THE PREFERRED EMBODIMENT

Figure 1:
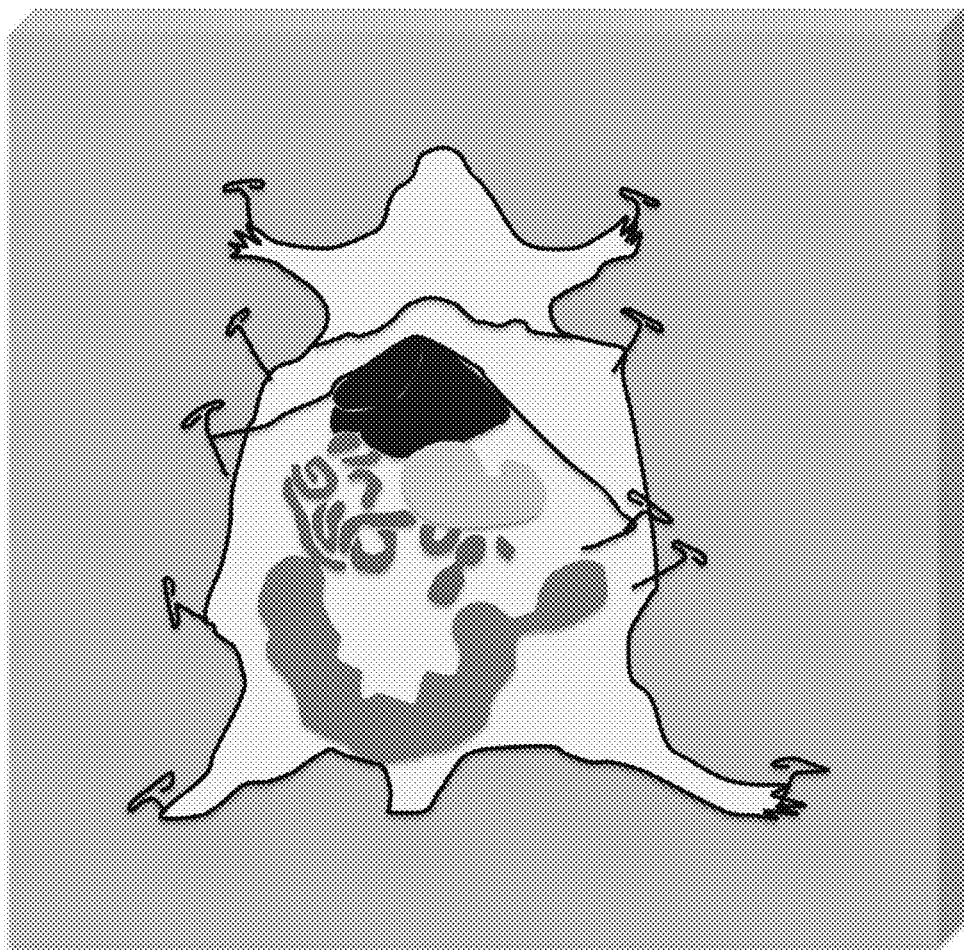
FIG. 1 depicts a conventional pinning methodology for mouse immobilization.
Figure 2:
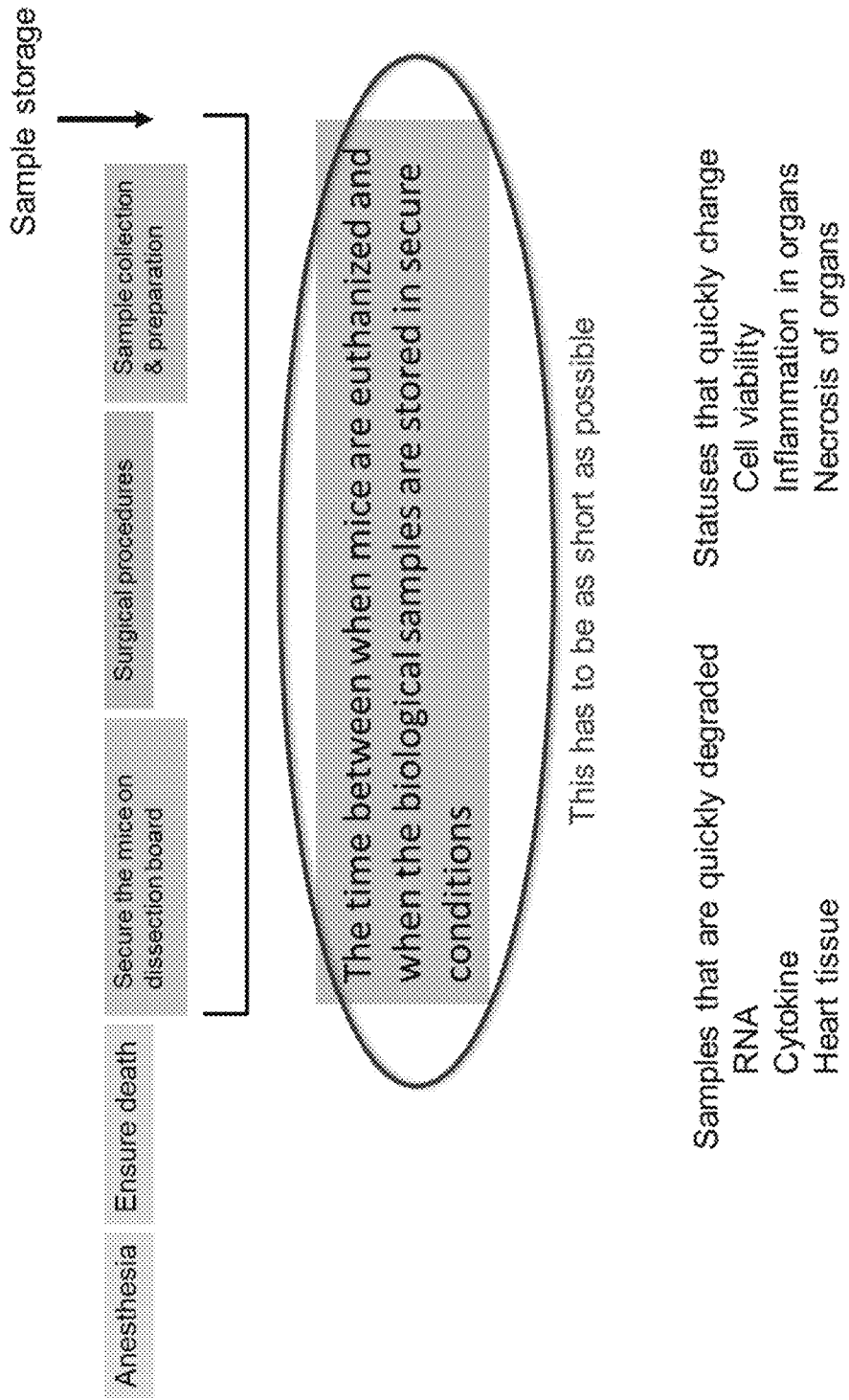
FIG. 2 depicts a timeframe of typical mouse dissection.
Figure 3C:
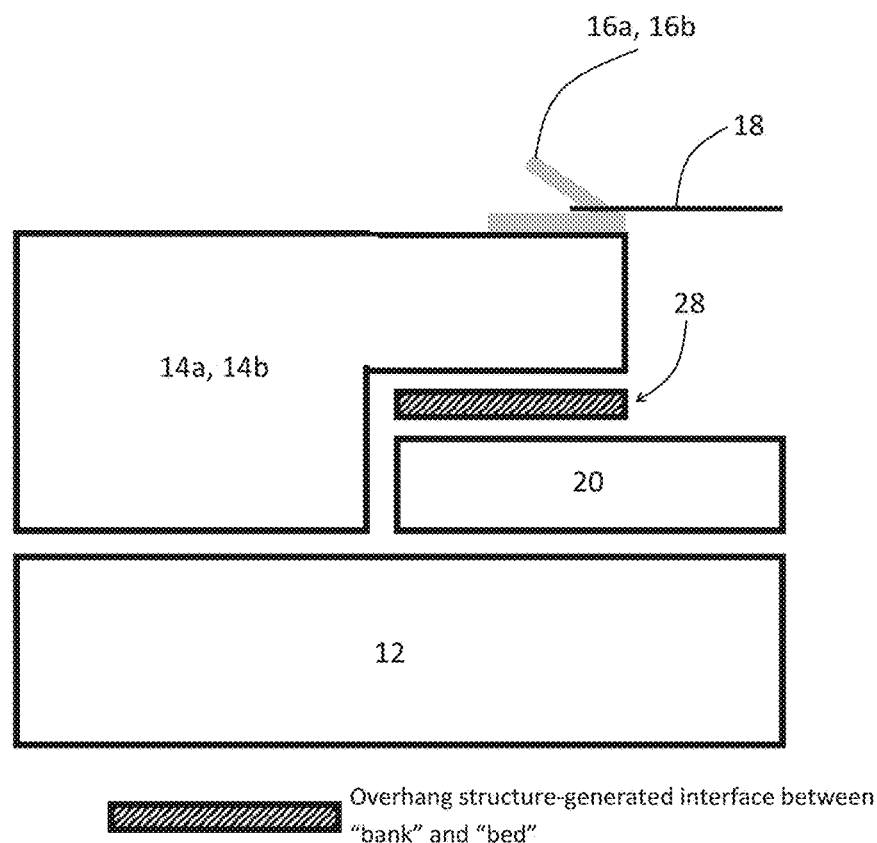
FIG. 3C is a close-up view of an overhang generated by each bank component in overlying relation to the bed component.
Figure 3D:
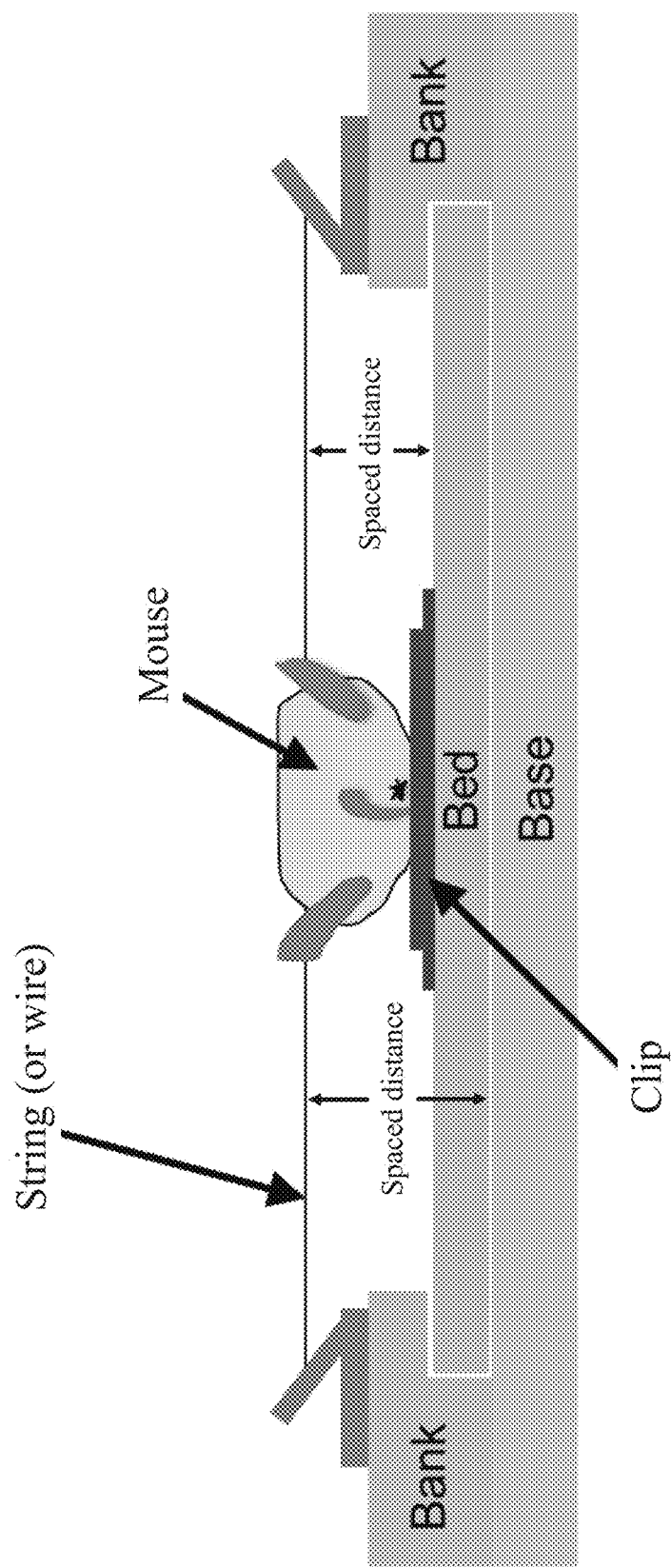
FIG. 3D is an end view of an embodiment of the current invention.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

In an embodiment, as can be seen in FIGS. 3A-3D, the current invention is a rodent immobilizing apparatus, generally denoted by the reference numeral 10, for use during experimental procedures, dissection, and sample procurement. Rodents include, but are not limited to, mice, rats, and hamsters.

As can be seen FIGS. 3A & B, apparatus 10 has two (2) points of adherence of the rodent to apparatus 10, one at the head/jaw region and one at the tail region of the rodent. Generally, rodent immobilizing apparatus 10 includes a main board and a dissection board. The main board includes base component 12, bank 14a disposed along one side of base component 12, bank 14b disposed along an opposite side of base component 12, string/wire hook module 16a disposed on bank 14a, string/wire hook module 16b disposed on bank 14b, and string/wire 18 disposed sufficiently taut between hooks 16a, 16b. The dissection board includes bed component 20 having leading edge 22a, and tail clamp 24 having open ends 26a, 26b.

When the main board and dissection board are engaged with each other, bed component 20 is positioned in overlying relation to base component 12 along a central axis of base component 12. Bed component 20 has a superior portion, in proximity to which the rodent's head is to be positioned, and an inferior portion, in proximity to which the rodent's rump and tail are to be positioned. Bed component 20 further includes superior (leading) edge 22a, and base component 12 includes inferior edge 22b and superior edge 22c.

Now referring to FIGS. 3A-3D, base component 12 and bed component 20 have corresponding left and right sides, where bank 14a is positioned in overlying relation to the left side of base component 12 and bank 14b is positioned in overlying relation to the right side of base component 12. Banks 14a, 14b are affixed (permanently or removably) to the top surface of base component 12 on each side of bed component 12, thus forming a lateral space between banks 14a, 14b atop base component 12.

Banks 14a, 14b have substantially parallel inner edges, such that bed component 20 is slidable along the parallel inner edges of the banks in overlying relation to base component 12 and in underlying relation to the overhangs of banks 14a, 14b. Each overhang structure generates an additional interface, generally denoted by reference numeral 28, between each bank 14a, 14b and bed component 20, and helps bed component 20 remain stable and stationary against any contraction force caused by the stretched rodent body. This can be most clearly seen in FIGS. 3C-3D. If bank 14a, 14b on each side of the main board does not have an overhang structure, then bed component 20 may move undesirably in a perpendicular or vertical direction. Overhang structure-generated interface 28 is designated by the patterned line in FIG. 3C.

In an alternative embodiment, banks 14a, 14b can be disposed in sliding relation to base component 12 and/or bed component 20, so that banks 14a, 14b can slide toward and away from the superior and inferior portions of apparatus 10. Banks 14a, 14b have similar dimensions and are parallel to each other, such that when one bank 14a slides in a direction, the other bank 14b slides as well in the same direction and the same amount.

String/wire hook (or clamp or other securing mechanism) 16a is affixed (permanently or removably) to the top surface of bank 14a; similarly, string/wire hook (or clamp or other securing mechanism) 16b is affixed (permanently or removably) to the top surface of bank 14b. Hooks 16a, 16b are coupled to their respective banks 14a, 14b in mirror relation to each other. For example, if one string/wire hook is x distance from the superior edge of its corresponding bank, the other string/wire hook is also x distance from the superior edge of its corresponding bank. Optionally, the string/wire hooks are each y distance from the inner edge of their corresponding banks.

String/wire 18 is an elongate, thin, flexible structure (e.g., fabric or metal thread, rod, or cable) that has two ends. One end of string/wire 18 is secured to hook 16a, and the opposite end of string/wire 18 is secured to hook 16b. String/wire 18 should be sufficiently taut that a structure can be hooked onto it and remain substantially stationary hooked thereon and sufficiently taut to also provide a variability to the distance between string/wire 18 and the top surface of bed component 20. In any case, string/wire 18 disposed between string/wire hooks 16a, 16b should be approximately perpendicular or transverse to the length of the rodent (i.e., the longitudinal axis of the apparatus) when positioned on bed component 20. Further, the positioning of hooks 16a, 16b atop banks 14a, 14b with string/wire 18 disposed therebetween results in a spaced distance being formed between string/wire 18 and the top surface of bed component 20, along with a spaced distance being formed between string/wire 18 and the top surface of base 12. This can be seen clearly in FIG. 3D.

An inferior portion of bed component 20 (i.e., proximal to where the rodent's rump would be positioned) includes tail clamp 24 or other mechanism that has an inherent downward or closed bias (relative to bed component 20) to hold the rodent's tail in place. As such, when tail clamp 24 is lifted or the downward force is otherwise removed from bed component 20, clamp 24 moves back toward the closed position when that upward force is removed. In this way, the rodent's tail can be secured within the clamp whether loose or taut.

Figure 4A:
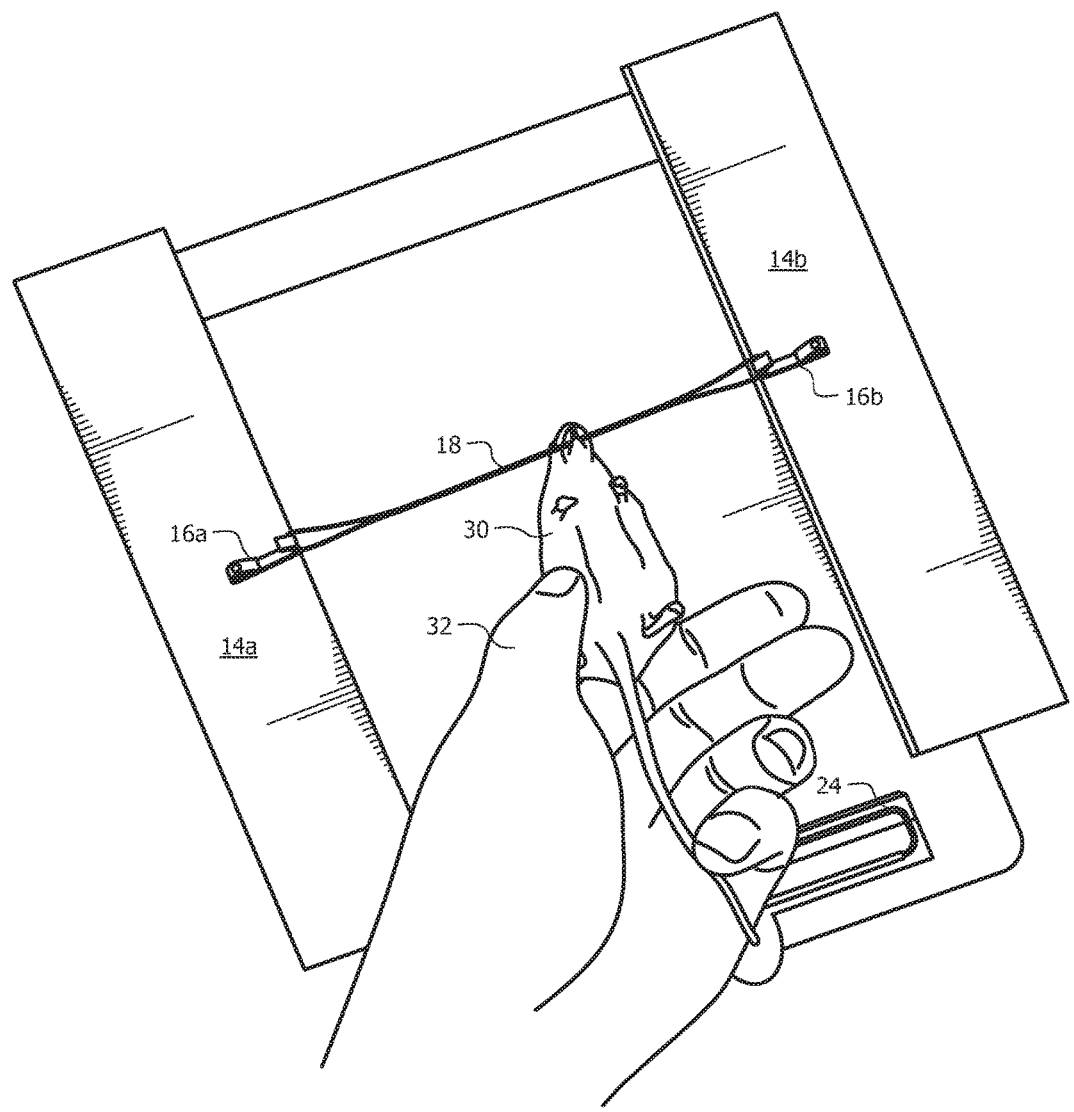
FIG. 4A depicts a step of hooking the rodent's teeth onto the string/wire, thus immobilizing the rodent's head region, according to an embodiment of the current invention.

In operation, as most clearly seen in FIGS. 4A-4D, an anesthetized and/or euthanized rodent, indicated by the reference numeral 30, is placed in supine position on bed component 20, and the maxillary incisor teeth of rodent 30 are hooked onto string/wire 18 bridged between banks 14a, 14b on each side of bed component 20, with the head portion of rodent 30 positioned within the spaced distance between string/wire 18 and bed component 20 (see FIG. 4A). Alternatively, upon positioning rodent 30 supine on bed component 20, bed component 20 can then slide superiorly until the head portion of rodent 30 is positioned within the spaced distance between string/wire 18 and bed component 20 and string/wire 18 is aligned with the jaw of rodent 30. String/wire 18 should be positioned within the jaw of rodent 30. In either case, though the former tends to be more effective, the rodent's head portion is thus held in place in that manner (between and under the rodent's teeth as well).

Further, in order to engage the dissection board (i.e., bed component 20) with the main board (i.e., base component 12 and banks 14a, 14b), superior (leading) edge 22a of the dissection board engages inferior edge 22b of the main board and slides along base component 12 between banks 14a, 14b toward superior edge 22c of the main board in the direction indicated by arrow 36 in FIG. 3A.

Figure 4B:
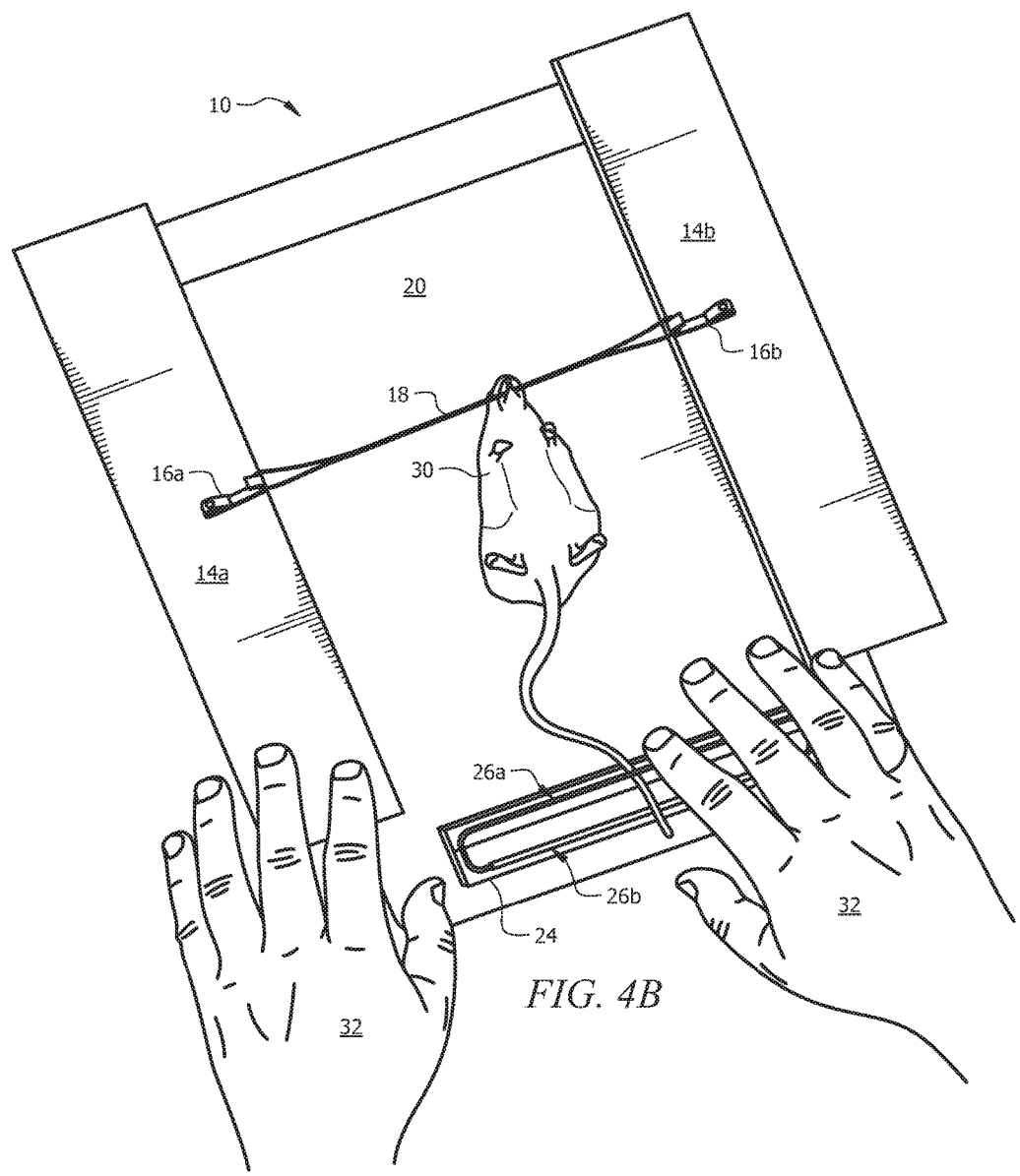
FIG. 4B depicts a step of clamping the rodent's tail, thus immobilizing the rodent's tail region.

Before or after the jaw of rodent 30 is hooked onto string wire 18, the tail of rodent 30 is positioned in tail clamp 26. Tail clamp 26 has open end 26a along the superior side of clamp 26 and open end 26b along the inferior side of clamp 26. This allows the tail of rodent 30 to be pulled through tail clamp 26, whether taut or slack, and clamp 26 is released to allow clamp 26 to stabilize and immobilize the tail of rodent 30 (FIG. 4B). This step of clamping the tail of rodent 30 can be performed before or after sliding bed component 20 along base component 12 and/or banks 14a, 14b.

Figure 4C:
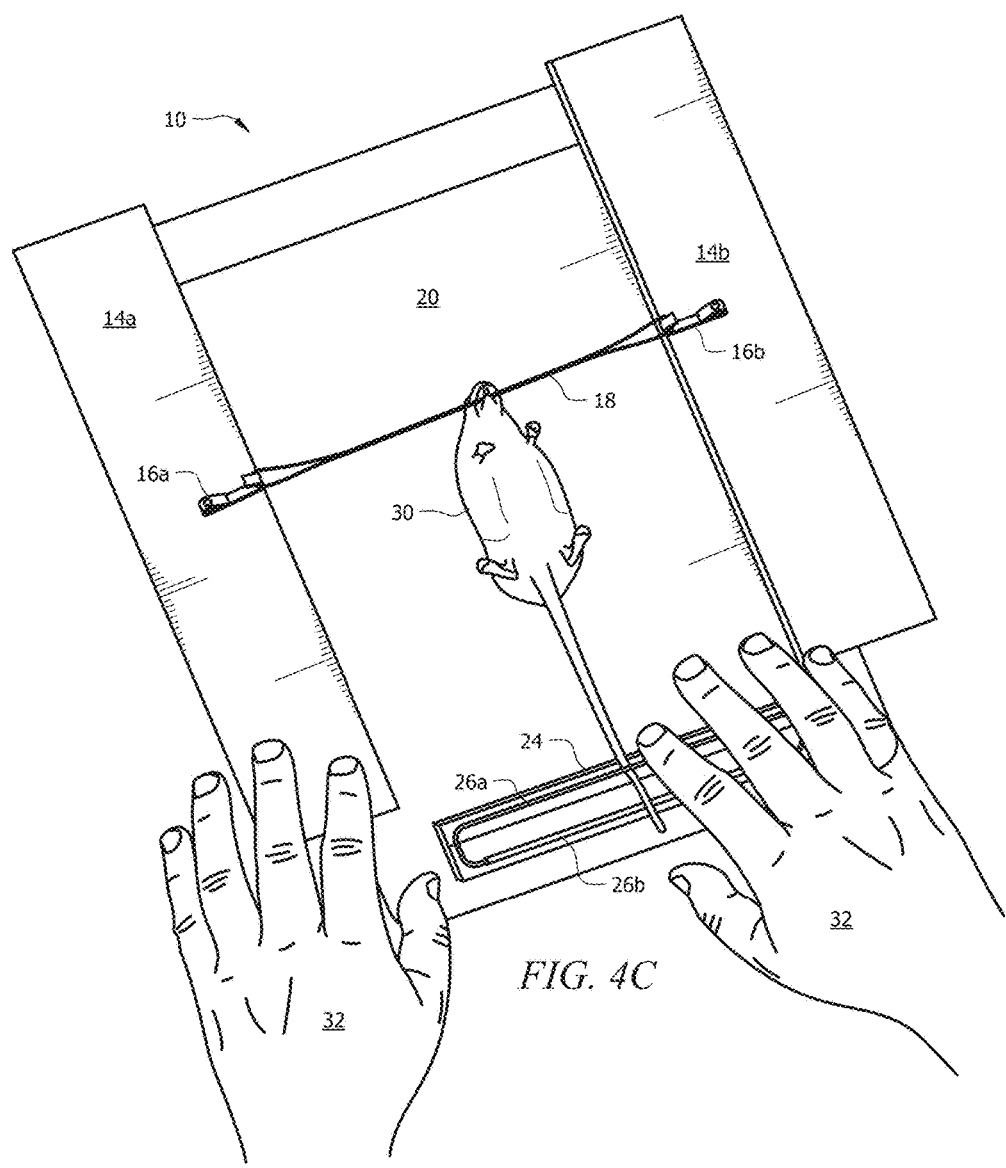
FIG. 4C depicts a step of pulling/sliding the bed component inferiorly to elongate/stretch the rodent out on the bed component.
Figure 4D:
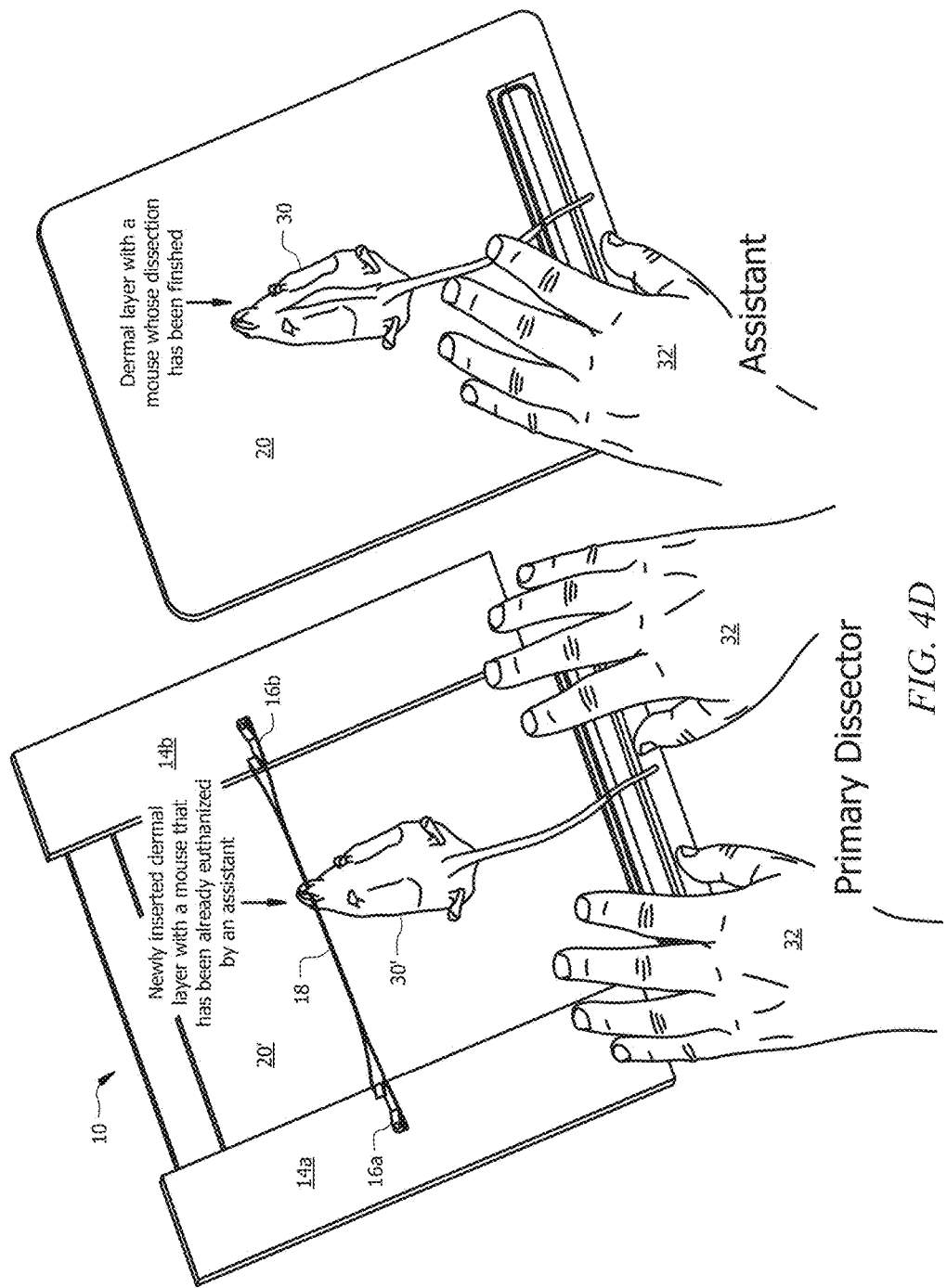
FIG. 4D depicts the ability to remove one rodent on a first bed component from the device and insert a new rodent on a second bed component into the device, for purposes of rapid dissection of both rodents and subsequent sample collection.

Bed component 20 can then be pulled inferiorly (away from superior edge 20c of the main board, in the direction indicated by arrow 34), so that the tail of rodent 30 is pulled taut (FIG. 4C). It should be noted that the head of rodent 30 remains immobilized due to string/wire 18 hooked around its maxillary incisor teeth, and the tail of rodent 30 remains immobilized due to tail clamp 24 holding its tail. By pulling bed component 20 (with rodent 30 thereon) inferiorly in the direction indicated by arrow 34 as much as possible, the dissector can ensure that rodent 30 is stretched well and is firmly immobilized on apparatus 10, specifically on bed component 20 between banks 14a, 14b. Additionally, the ability to pull bed component 20 inferiorly allows the dissector to use apparatus 10 for mice of varying sizes, from small to large and from one dissection/sample collection to the next. This variability will become clearer as this specification continues.

In this way, rodent 30 as a whole is immobilized entirely and rapidly. When the dissection is complete and/or the sample collected from rodent 30, rodent 30 can be rapidly removed from apparatus 10, and a new rodent, indicated by the reference numeral 30', can be positioned and immobilized within apparatus 10. This can be accomplished, for example, by unhooking string/wire 18 from the teeth of rodent 30 and sliding bed component 20 entirely out of base component 12 and banks 14a, 14b since bed component 20 is separable from the main board (base component 12 and banks 14, 14b). Bed component 20 can then be given to an assistant or other member of the team to clean rodent 30, complete the sample collection, etc. This can be seen in FIG. 4D. The primary dissector can then immediately proceed with second/subsequent anesthetized/euthanized rodent 30' by inserting second bed component 20' with rodent 30' thereon. If rodent 30' can be pre-prepared by having its tail secured within clamp 24, then the dissector simply needs to slide bed component 20' along base component 12 and banks 14a, 14b, hook string/wire 18 on the teeth of rodent 30', and pull bed component 20' inferiorly to stretch rodent 30' out, similar to that described with rodent 30. In this way, rodent 30' is very quickly ready for dissection/sample collection. If second rodent 30' is bigger or smaller than first rodent 30, bed component 20' would simply be pulled inferiorly more (if rodent 30' is larger than rodent 30) or less (if rodent 30' is smaller than rodent 30) than bed component 20.

Figure 5A:
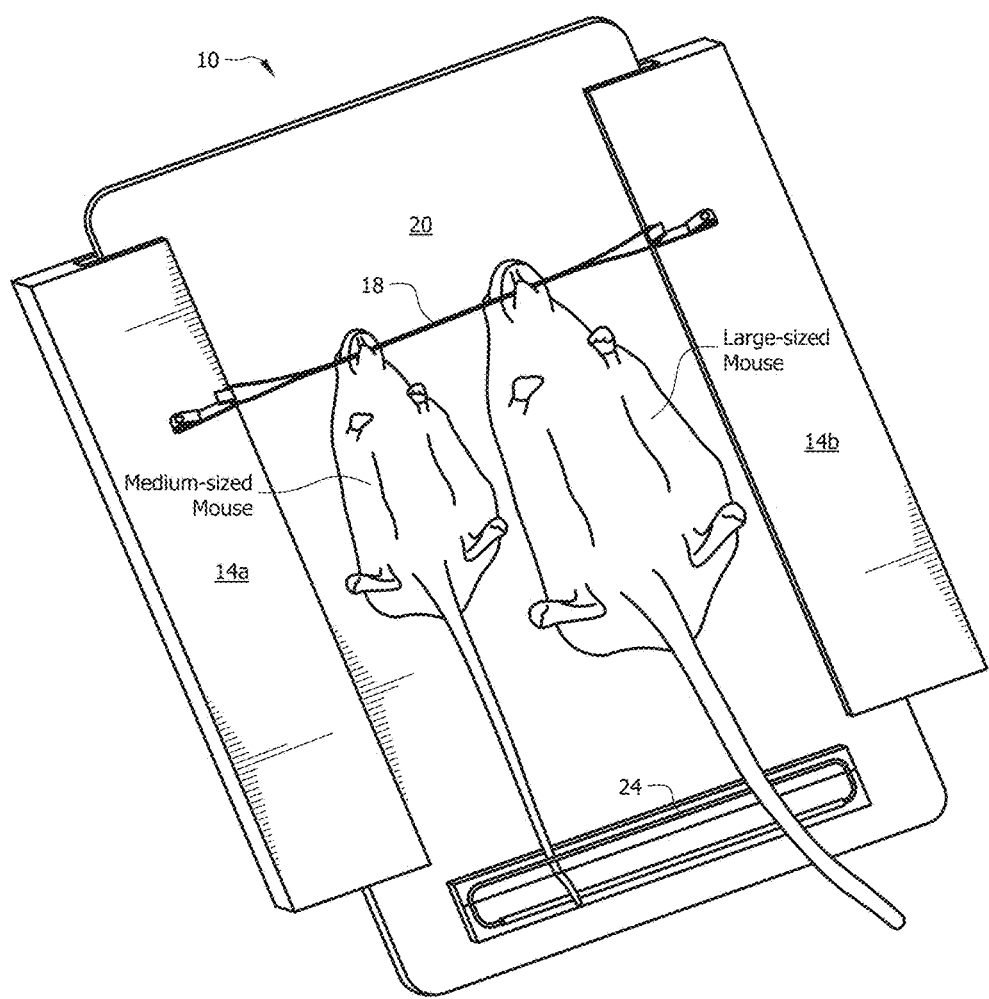
FIG. 5A depicts a medium-sized mouse and a large-sized mouse adjacent to each other with the current apparatus in a setup for the medium-sized mouse.
Figure 5B:
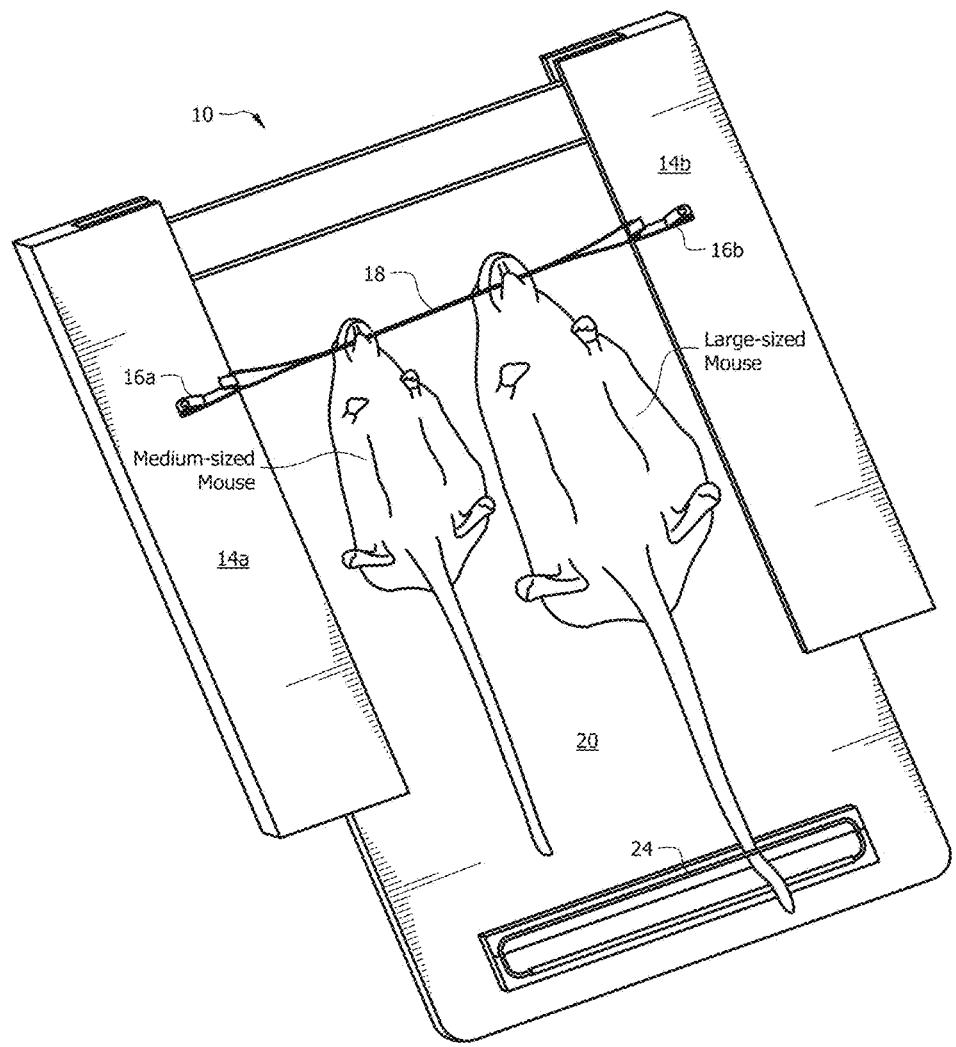
FIG. 5B depicts a medium-sized mouse and a large-sized mouse adjacent to each other with the current apparatus in a setup for the large-sized mouse.
Figure 6A:
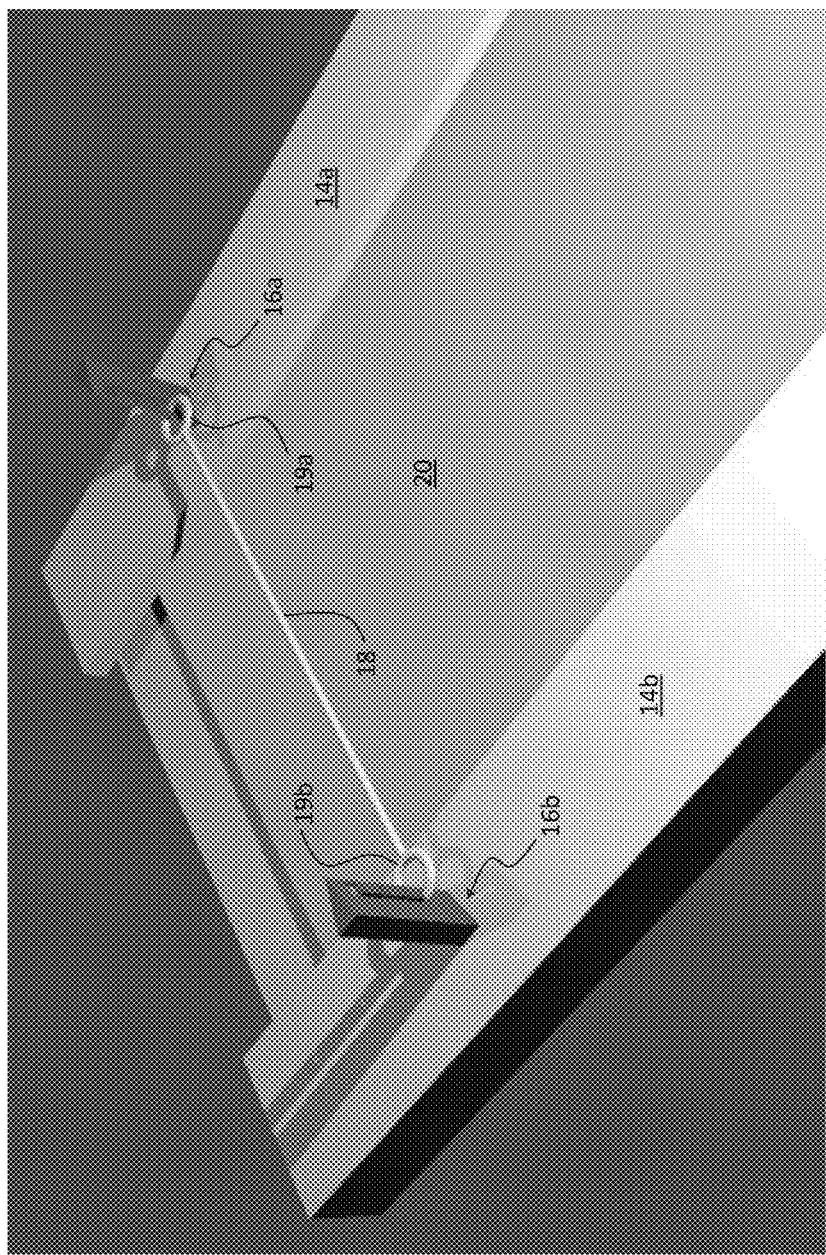
FIG. 6A is a perspective view of an embodiment of the current invention using an alternate type of string/wire hook module.
Figure 6B:
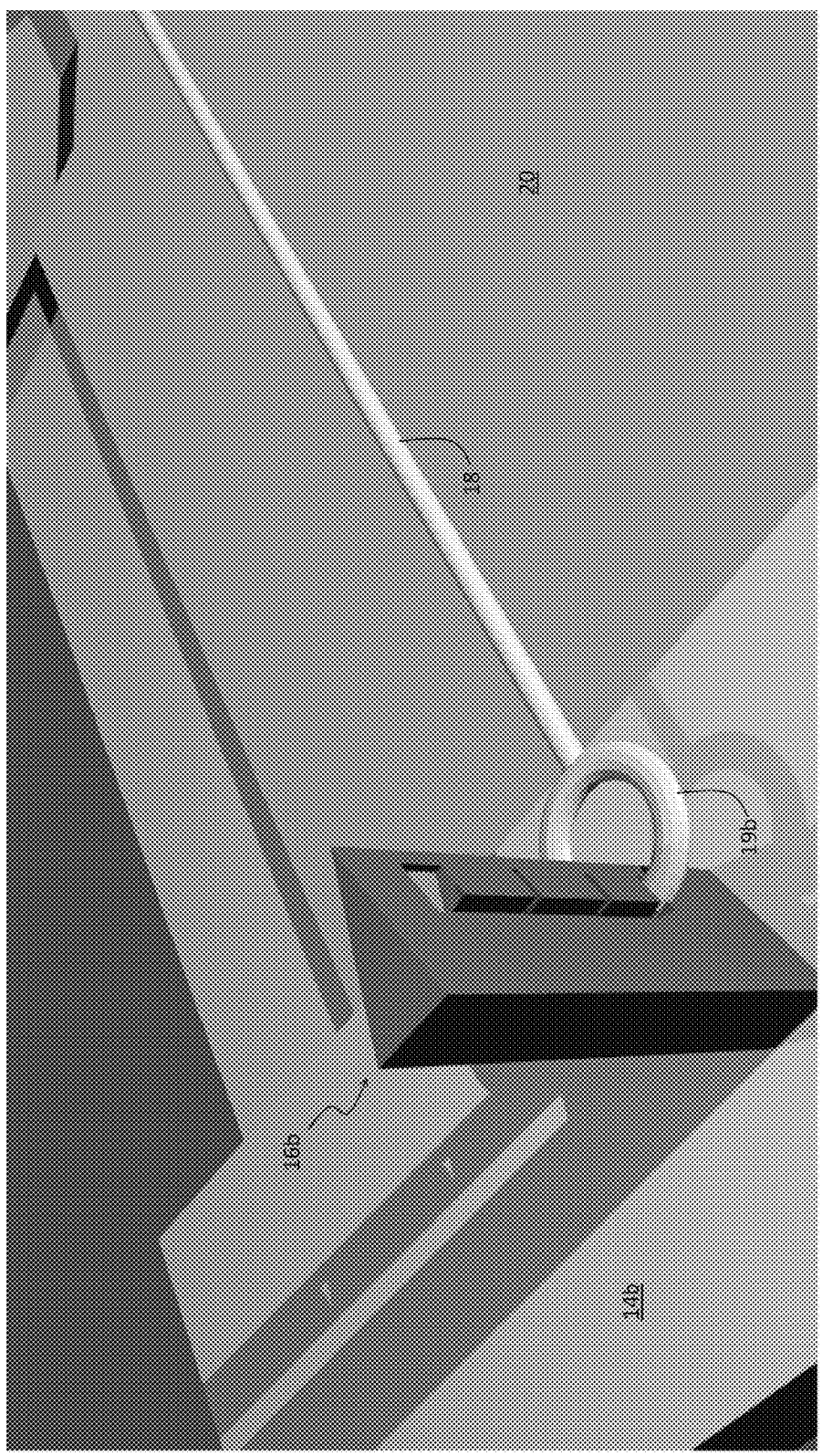
FIG. 6B is a close-up perspective view of the hook module of FIG. 6A.
Figure 6C:
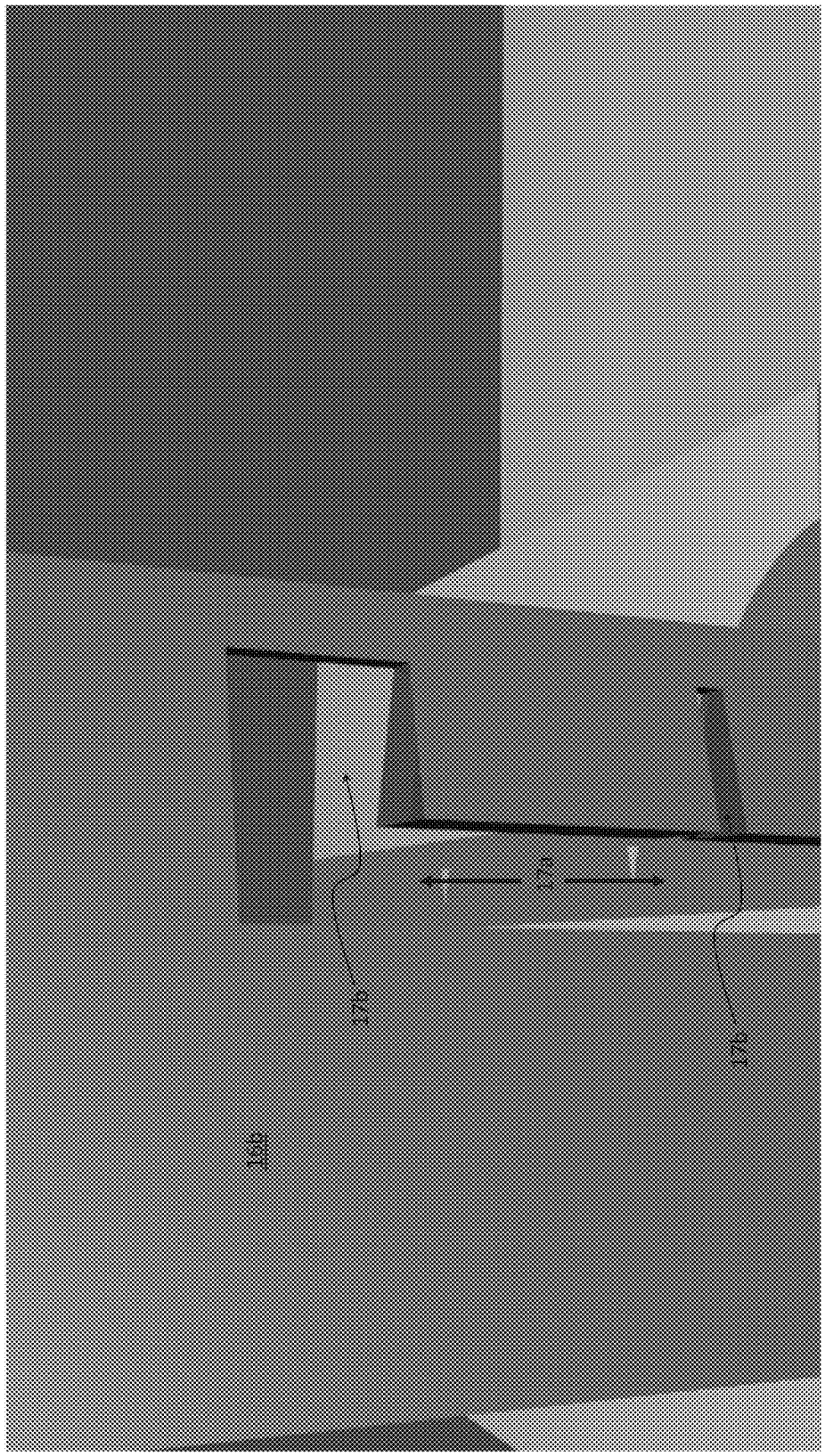
FIG. 6C is a close-up view near the top of the hook module of FIG. 6A.
Figure 6D:
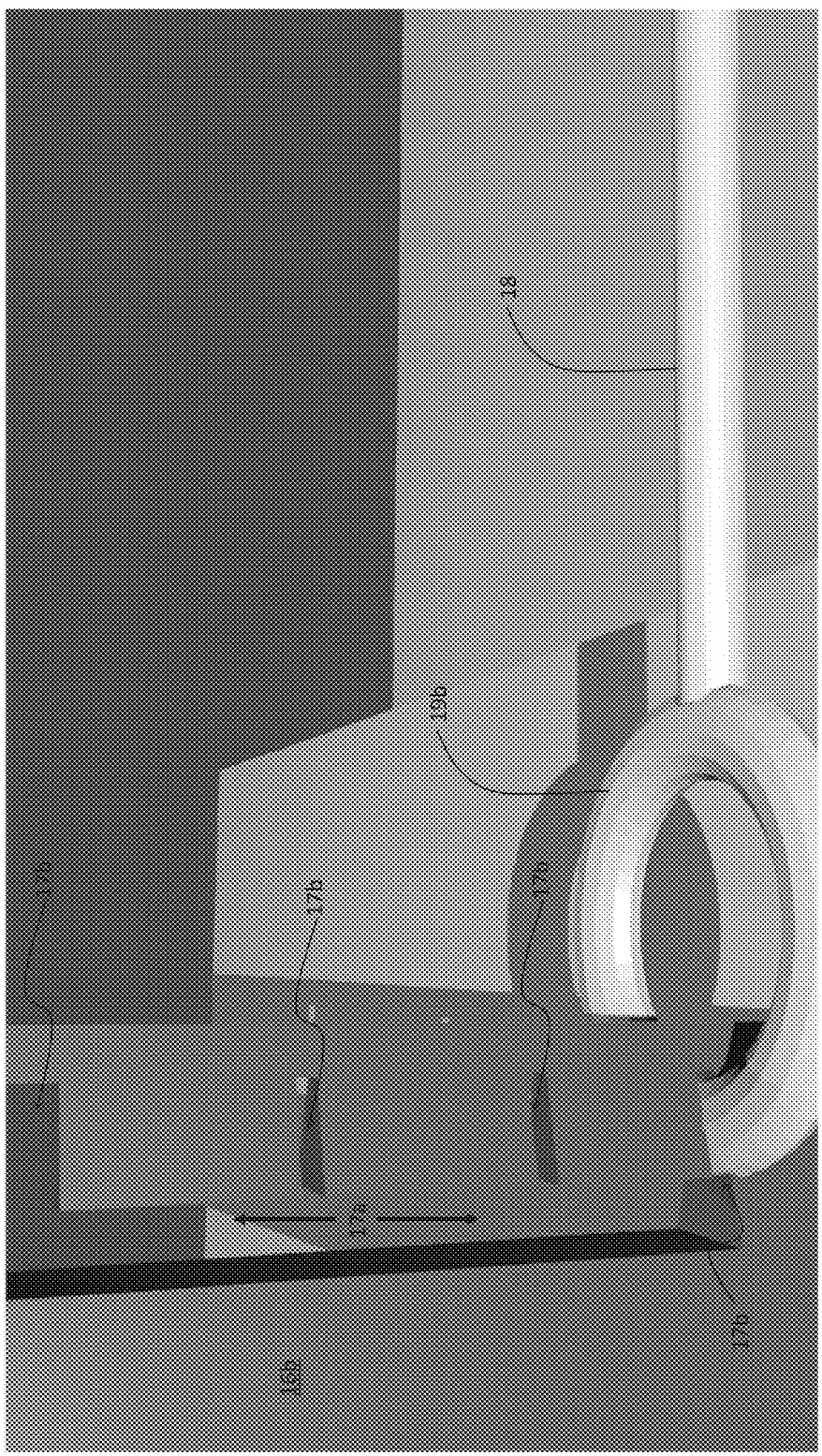
FIG. 6D is a close-up view near the bottom of the hook module of FIG. 6A.
Figure 7A:
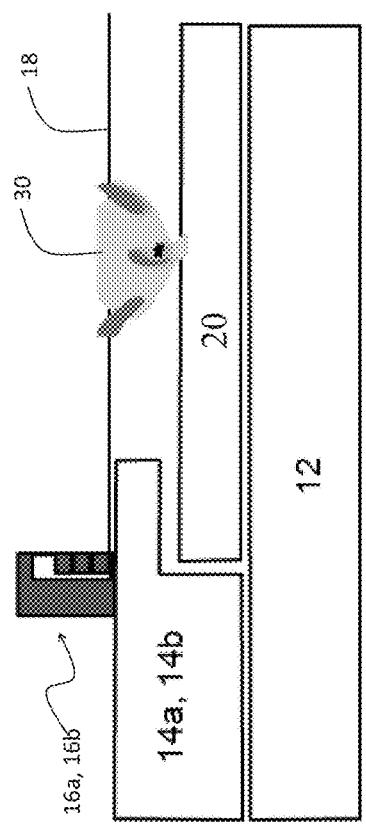
FIG. 7A is an end schematic view of an embodiment of the current invention, using the alternate string/wire hook module, with a smaller mouse.
Figure 7B:
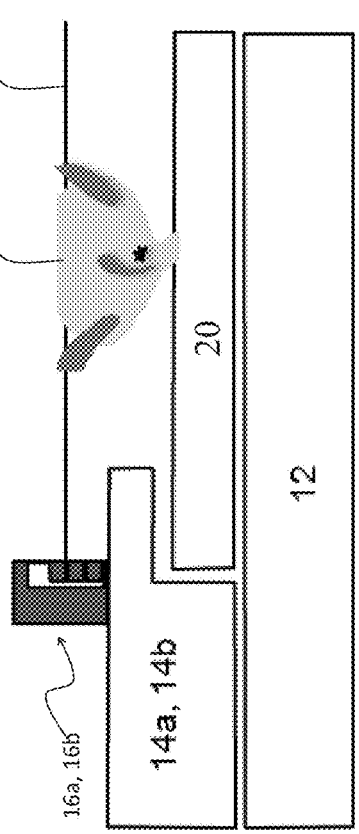
FIG. 7B is an end schematic view of an embodiment of the current invention, using the alternate string/wire hook module, with a larger mouse.
Figure 8:
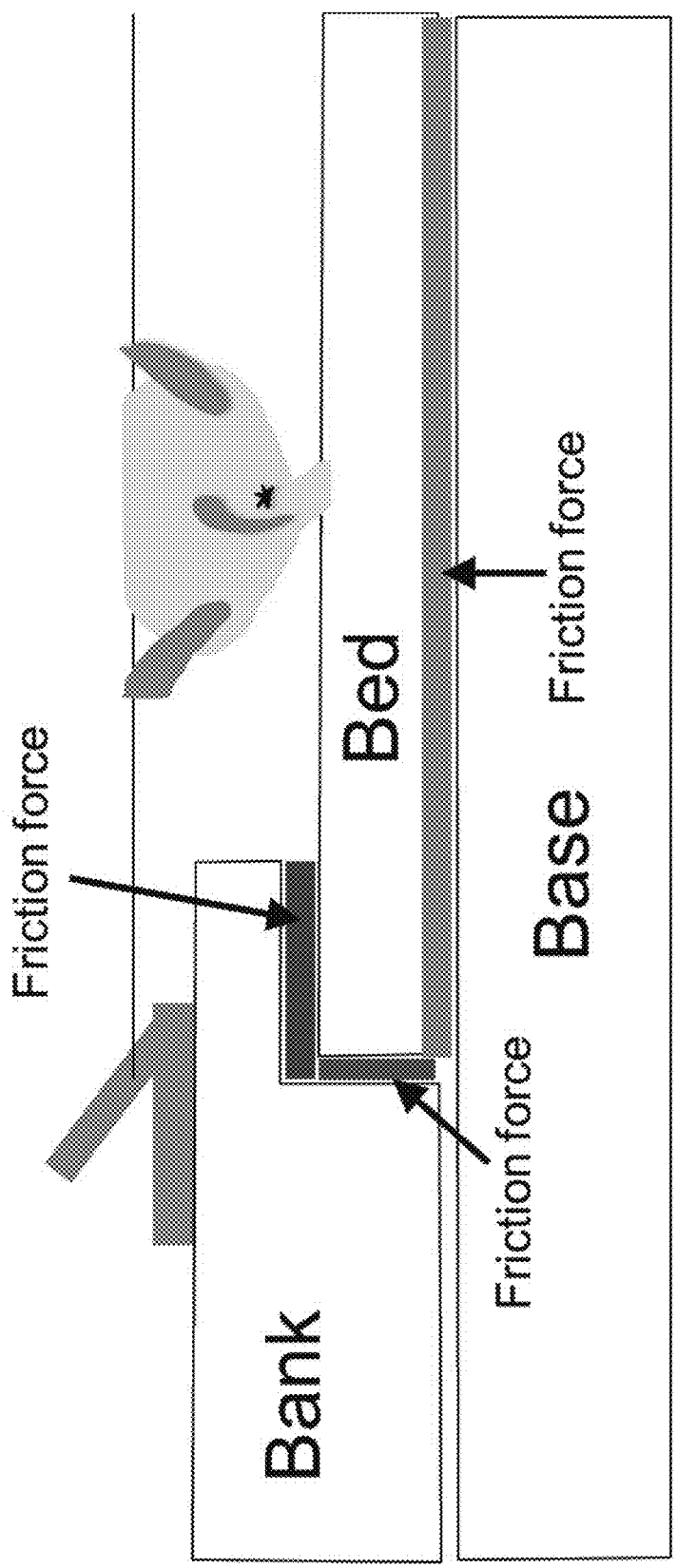
FIG. 8 is an end schematic view of an embodiment of the current invention showing the friction forces that maintain stability of the overall apparatus during operation.

As noted, the sliding mechanism of bed component 20 along base component 12 and banks 14a, 14b allows different-sized rodents to be immobilized on apparatus 20 (see FIGS. 5A-5B). In FIG. 5A, a medium-sized rodent is positioned adjacent to a large-sized rodent where the medium-sized rodent is immobilized on apparatus 10 and the large-sized rodent can be seen to be too large for that particular configuration of apparatus 10. In FIG. 5B, a medium-sized rodent is positioned adjacent to a large-sized rodent where the large-sized rodent is immobilized on apparatus 10 and the medium-sized rodent can be seen to be too small for that particular configuration of apparatus 10.

In practice, a dissector utilizes just a few seconds (~5 seconds) to immobilize rodent 30 on apparatus 10 and even less time (<5 seconds) to remove rodent 30 from apparatus 10 after dissection/sample collection. This time period is compared to the minutes it can take to secure and remove a rodent from a dissection board in the conventional pin/tape manner, such as that seen in FIG. 1.

Apparatus 10 may also be modular, such that each component is separable from the other components, so that when a component has worn out or become damaged, that component by itself can be replaced with a new one. For example, if bank 14a or string/wire hook 16b needed replacement, each could be individually uncoupled from apparatus 10 and replaced accordingly. Alternatively, various components-such as base 12, bank 14a, and bank 14b—may be fabricated as a single piece to facilitate an easier cleanup procedure.

Further, the material of each functional component can be optimized according to each dissector, e.g., wood, plastic, metals, or other suitable materials.

It can be understood that in certain embodiments, base component 12 may not even be need to be included with apparatus 10. For example, banks 14a, 14b can be secured to a table top (rather than to the top surface of base component 12). This would still allow bed component 20 to slide between banks 14a, 14b and immobilization of rodent 30 on bed component 20 via string/wire 18 at the head portion of rodent 30 and tail clamp 24 at the tail portion of rodent 30.

In certain embodiments, as seen in FIGS. 6A-6D and 7A-7B, string/wire hook module 16a, 16b may be somewhat columnar in form with vertical channel 17a disposed therein, along with a plurality of divots 17b extending therefrom toward the opposite hook module. In this way, string/wire 18 may or may not include ring 19, or other hooking mechanism, to engage one of divots 17b. Alternatively, string/wire 18 can just be threaded through divot 17b and secured in place, for example through the topmost divot, which can be larger than the others.

Divots 17b being vertically spaced apart along vertical channel 17a permits additional height adjustability of string/wire 18 to fit different sizes of rodents 30. See FIGS. 7A-7B for an indication as to how the vertical spaced distance between string/wire 18 and bed component 20 can be changed based on which divot 17b that string/wire 18 engages.

To maintain stability of apparatus 10 when pulling bed component 20 inferiorly with rodent 30 disposed thereon, it is contemplated herein that the friction forces between bed component 20 and banks 14a, 14b, along with the friction force between bed component 20 and base 12, counteract the force generated by the stretched body of rodent 20. If additional stability of apparatus 10 is desired, typical mechanisms can be used, such as suction cups or adhesives on the bottom surface of base 12.

GLOSSARY OF CLAIM TERMS

Bank: This term is used herein to refer to a ridge or other structural component that is raised above a surrounding level.

Base component: This term is used herein to refer to a bottom or lower component of an apparatus on which other components of the apparatus would be positioned.

Bed component: This term is used herein to refer to a flat surface on which a rodent can be laid in a supine position.

Diametric opposition: This term is used herein to refer to two (2) structures being positioned on the opposite sides of a fixed length/distance.

Divot: This term is used herein to refer to an indentation, notch, recess or channel disposed along a flat surface.

Empty area: This term is used herein to refer to an extent of surface between two points that is clear of any obstructions that would hinder the activity needed to be performed within that extent of surface.

Force: This term is used herein to refer to an interaction that on a component that changes the motion of that component.

Hook or clamp module: This term is used herein to refer to any mechanism that is capable of securing a string or wire thereto.

Horizontal spaced distance: This term is used herein to refer to a physical, spatial extent between two points (e.g., two banks) in the x direction.

Inferior: This term is used herein to refer to a portion of a structure closer to where a rodent's tail or rump would be disposed when supine.

Inherent downward bias: This term is used herein to refer to an inclination or predisposition in a downward/closed direction. For example, a tail clamp disposed on a bed component may have a structural predisposition downward toward the bed component.

Length: This term is used herein to refer to the extent or distance of one or more components in the y direction (e.g., from the inferior edge of the base component to the superior edge of the base component).

Overhang component: This term is used herein to refer to that portion of a structure that protrudes over a base or other part thereunder.

Rodent: This term is used herein to refer to any mammal of the order Rodentia, for example including, but not limited to, mice, rats, squirrels, prairie dogs, porcupines, beavers, guinea pigs, and hamsters.

Stretch out: This term is used herein to refer to fully extending a rodent or body parts thereof (e.g., torso, legs, etc.), for example by pulling.

String or wire: This term is used herein to refer to an elongate, thin, and flexible structure/thread/cable that can hook into a rodent's jaw or teeth.

String-to-clamp distance: This term is used herein to refer to an extent along the current rodent immobilization apparatus between the string or wire to the tail clamp. This distance is adjustable based on the size of the rodent and slidable positioning of the bed component.

Substantially parallel: This term is used herein to refer to two (2) edges/sides being equally distance from each other along their lengths, to the extent that an insertable component can slide along the edges/sides without hindrance. It can be understood that this can be accomplished without the edges/sides being completely parallel.

Substantially perpendicular: This term is used herein to refer to two (2) components forming a right angle or an angle very close to a right angle. It can be understood that the string/wire and bank lengths do not need to be perfectly perpendicular in order to hook into a rodent's jaw or teeth.

Sufficiently taut: This term is used herein to refer to a string or wire having a particular tension (whether taut or slackened), such that the string or wire can confer a variability to the distance between the string and underlying surface. The flexibleness of the string and resultant variable distance makes the procedure of hooking the rodent's jaw/teeth thereon easier and also facilitates the apparatus being adjustable for rodents with different sizes. It can be understood that the tension of the string/wire can change based on the type of hook/clamp module used. For example, if the hook/clamp module permits adjustability of the string/wire, as in FIGS. 6A-6D and 7A-7B, then the string/wire may be relatively tauter than if the hook/clamp module was a singular, single hook on each bank. In order words, the tension, or lack thereof, on the string or wire must be sufficient just to impart the variability needed to adjust for rodents with different sizes.

Superior: This term is used herein to refer to a portion of a structure closer to where a rodent's head would be disposed when supine.

Tail clamp: This term is used herein to refer to a clasp or other suitable mechanism for securing or immobilizing a rodent's tail.

Vertical spaced distance: This term is used herein to refer to a physical, spatial extent between two points (e.g., base surface and string/wire) in the z direction.

Width: This term is used herein to refer to the extent or distance of one or more components in the x direction (e.g., from the inner edge of one bank to the inner edge of the other bank).

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A rodent immobilization apparatus for a survival or non-survival surgical procedure on a rodent, or postmortem sample collection from said rodent, comprising:
   a first raised bank having a length between a first end and a second end, said first bank also having a straight inner edge along said length;
   a second raised bank having a length between a first end and a second end, said second bank also having a straight inner edge along said length;
   said second bank is disposed a horizontal spaced distance away from said first bank, thus forming an empty area between said inner edges of said first and second banks, said empty area extends continuously the entire length of said first and second banks;
   said inner edges of said first and second banks are substantially parallel to each other,
   said first and second banks each further including an overhang component that extends further into said empty area than said inner edges of said first and second banks, said overhang component of said first and second banks extending toward each other, said overhang components are spaced away from each other to form a space within said empty area, said space extending along the length of said first and second banks;
   a first hook or clamp module disposed in overlying relation to said first bank at a position closer to said first end of said first bank;
   a second hook or clamp module disposed in overlying relation to said second bank at a position closer to said first end of said second bank, said second hook or clamp module being disposed in diametric opposition to said first hook or clamp module across said empty area;
   a string or wire having a first point secured to said first hook or clamp module and a second point secured to said second hook or clamp module, such that said string or wire is sufficiently taut and disposed across said empty area, wherein said sufficiently taut string or wire is disposed substantially perpendicular to the length of said first and second banks;
   a flat base component disposed in underlying relation to said first and second banks, said flat base component defines a surface on which said first and second banks are positioned;
   a vertical spaced distance formed between said string or wire and said surface of said flat base component;
   a flat bed component having a length and a width, said width being slightly smaller than a width of said empty area;
   said flat bed component is received within the empty area, wherein said bed component is slidable on said surface along said inner edges of said first and second banks with said overhang component of said first bank disposed in overlying relation to one side of said bed component and said overhang component of said second bank disposed in overlying relation to an opposite side of said bed component, thus creating additional interfaces between said bed component and said first and second banks to stabilize said bed component between said first and second banks,
   a tail clamp is disposed on an inferior portion of said bed component closer to said second ends of said first and second banks, said tail clamp having an open superior side and an open inferior side,
   said bed component has a surface positioned in said space that is sized to receive a rodent thereon, said string or wire is configured to hook into a tooth of said rodent, and said tail clamp is configured to receive a tail of said rodent through said open superior and inferior sides to immobilize said tail of said rodent; and
   a string-to-clamp distance formed between said string or wire and said tail clamp, wherein said string-to-clamp distance and a size of said rodent have a direct relationship to each other, such that as said size of said rodent increases, said string-to-clamp distance increases as well,
   wherein upon said rodent is positioned supine on said surface of said bed component within said space, said string or wire is hooked into said tooth of said rodent, and said tail clamp immobilizes said tail of said rodent, said bed component can slide away from said string or wire toward said second end of said first and second banks to stretch said rodent on said bed component.

2. A rodent immobilization apparatus as in claim 1, wherein said surface on which said bed component is slidable and said first and second banks are positioned is a top surface of said base component.

3. A rodent immobilization apparatus as in claim 2, wherein said overhang component of said first and second banks is a flange in overlying relation to said base component and said bed component.

4. A rodent immobilization apparatus as in claim 2, wherein said apparatus is modular in that said base component, said first bank, said second bank, said first hook or clamp module, said second hook or clamp module, said string or wire, and said bed component are separable from each other.

5. A rodent immobilization apparatus as in claim 1, wherein said first and second points of said string or wire are respective ends of said string or wire.

6. A rodent immobilization apparatus as in claim 1, further comprising:

said tail clamp having an inherent downward bias relative to said bed component to hold said tail of said rodent in place, such that said tail is positioned within said clamp when a force acts upon said clamp to overcome said bias, and said clamp immobilizes said tail of said rodent when said force is removed.

7. A rodent immobilization apparatus as in claim 1, further comprising:

said first and second hook or clamp modules each being a column with a vertical channel disposed therethrough and a plurality of horizontally-extending, vertically-spaced divots extending therefrom, said string or wire being secured within one of said plurality of divots to extend across said empty area.

8. A rodent immobilization apparatus as in claim 7, wherein a top divot of said plurality of divots being a large window through which said string or wire can be threaded.

9. A rodent immobilization apparatus as in claim 7, wherein said string or wire includes a ring at said first and second points for securing within a divot in said each hook or clamp module.

* * * * *